US010166001B2

(12) United States Patent
An et al.

(10) Patent No.: US 10,166,001 B2
(45) Date of Patent: Jan. 1, 2019

(54) TRENDING S1 HEART SOUNDS AMPLITUDES IN AMBULATORY PATIENTS FOR WORSENING HF DETECTION (71) Applicant: Cardiac Pacemakers, Inc., St. Paul, MN (US)

(72) Inventors: Qi An, Blaine, MN (US); Pramodsingh Hirasingh Thakur, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 37 days.

(21) Appl. No.: 15/334,388

(22) Filed: Oct. 26, 2016

(65) Prior Publication Data

US 2017/0112463 A1 Apr. 27, 2017

Related U.S. Application Data (60) Provisional application No. 62/246,604, filed on Oct. 27, 2015.

(51) Int. Cl.
*A61B 5/02* (2006.01)
*A61B 7/02* (2006.01)
*A61B 5/0402* (2006.01)
*A61B 5/00* (2006.01)
*A61B 5/0205* (2006.01)
*A61B 5/053* (2006.01)
*A61B 5/08* (2006.01)
*A61B 5/091* (2006.01)
*A61B 5/0245* (2006.01)

(52) U.S. Cl.
CPC .............. *A61B 7/02* (2013.01); *A61B 5/0205* (2013.01); *A61B 5/0402* (2013.01); *A61B 5/7275* (2013.01); *A61B 5/746* (2013.01); *A61B 5/0245* (2013.01); *A61B 5/053* (2013.01); *A61B 5/0816* (2013.01); *A61B 5/091* (2013.01)

(58) Field of Classification Search
None
See application file for complete search history.

(56) References Cited

U.S. PATENT DOCUMENTS

6,076,015 A 6/2000 Hartley et al.
6,527,729 B1 3/2003 Turcott
8,364,263 B2 1/2013 Patangay et al.
(Continued)

*Primary Examiner* — Erica Lee
(74) *Attorney, Agent, or Firm* — Schwegman Lundberg & Woessner, P.A.

(57) ABSTRACT

An apparatus comprises a cardiac signal sensing circuit, a heart sound sensing circuit, and a signal processing circuit. The cardiac signal sensing circuit is configured to sense a plurality of cardiac signals representative of electrical cardiac activity of a subject. The heart sound sensing circuit is configured to sense a plurality of unfiltered heart sound signals representative of intrinsic mechanical cardiac activity of the subject. The signal processing circuit is configured to: detect an R-wave in a sensed cardiac signal and initiate a measurement window in a time relationship to the detected R-wave; determine amplitude of an S1 heart sound using a heart sound signal sensed during the measurement window; trend S1 heart sound amplitudes determined for the plurality of the unfiltered heart sound signals; and generate an alert when the trended S1 heart sound amplitude decreases below a threshold amplitude value.

17 Claims, 8 Drawing Sheets

(56) References Cited

U.S. PATENT DOCUMENTS

| | | |
|---|---|---|
| 8,700,149 B2 | 4/2014 | Patangay et al. |
| 8,972,008 B2 | 3/2015 | Patangay et al. |
| 2006/0116733 A1* | 6/2006 | Gunderson .......... A61N 1/3704 607/27 |
| 2008/0177194 A1 | 7/2008 | Zhang et al. |
| 2011/0015702 A1* | 1/2011 | Ternes ................. A61B 5/0255 607/62 |
| 2012/0158089 A1* | 6/2012 | Bocek ...................... A61N 1/37 607/28 |
| 2014/0276164 A1* | 9/2014 | Thakur .................. A61B 5/686 600/528 |
| 2015/0142071 A1 | 5/2015 | Min |
| 2015/0157260 A1* | 6/2015 | Zhang ................... A61M 5/172 600/323 |
| 2015/0343223 A1* | 12/2015 | Thakur .............. A61B 18/1206 604/66 |
| 2016/0025485 A1* | 1/2016 | Carlier ................... F28G 15/00 165/11.1 |

* cited by examiner

TRENDING S1 HEART SOUNDS AMPLITUDES IN AMBULATORY PATIENTS FOR WORSENING HF DETECTION

CLAIM OF PRIORITY

This application claims the benefit of priority under 35 U.S.C. § 119(e) of U.S. Provisional Patent Application Ser. No. 62/246,604, filed on Oct. 27, 2015, which is herein incorporated by reference in its entirety.

BACKGROUND

Ambulatory medical devices include implantable medical devices (IMDs), wearable medical devices, handheld medical devices, and other medical devices. Some examples of IMDs include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy or to aid a physician or caregiver in patient diagnosis through internal monitoring of a patient's condition. Some implantable medical devices can be diagnostic-only devices, such as implantable loop recorders (ILRs) and subcutaneously implantable heart failure monitors (SubQ HFMs). The devices may include electrodes in communication with one or more sense amplifiers to monitor electrical heart activity within a patient, or can include one or more sensors to monitor one or more other internal patient parameters. Subcutaneously implantable devices may include electrodes that are able to sense cardiac signals without being in direct contact with the patient's heart. Other examples of IMDs include implantable drug delivery systems or implantable devices with neural stimulation capability (e.g., vagus nerve stimulator, baroreflex stimulator, carotid sinus stimulator, spinal cord stimulator, deep brain stimulator, etc.).

Some examples of wearable medical devices include wearable cardioverter defibrillators (WCDs) and wearable diagnostic devices (e.g., an ambulatory monitoring vest, holter monitor, cardiac event monitor, or mobile cardiac telemetry devices). WCDs can be monitoring devices that include surface electrodes. The surface electrodes may be arranged to provide one or both of monitoring to provide surface electrocardiograms (ECGs) and delivery of cardioverter and defibrillator shock therapy. In some examples, a wearable medical device can also include a monitoring patch worn by the patient such as an adherable patch or can be included with an article of clothing worn by the patient.

Some examples of handheld medical devices include personal data assistants (PDAs) and smartphones. The handheld devices can be diagnostic devices that record an electrocardiograph (ECG) or other physiological parameter while the device is resting in the patient's hand or being held to the patient's chest.

Some medical devices include one or more sensors to monitor different physiologic aspects of the patient. The devices may derive measurements of hemodynamic parameters related to chamber filling and contractions from electrical signals provided by such sensors. Sometimes patients who are prescribed these devices have experienced repeated heart failure (HF) decompensation or other events associated with worsening HF. Symptoms associated with worsening HF include pulmonary and/or peripheral edema, dilated cardiomyopathy, or ventricular dilation. Early attention to signs and symptoms of HF decompensation is needed for the health of the patient and allows early initiation of treatment.

OVERVIEW

This document relates generally to systems, devices, and methods that monitor a physiological condition of a patient or subject. In particular it relates to systems, devices, and methods that detect onset of an acute heart failure event.

An apparatus example includes a cardiac signal sensing circuit, a heart sound sensing circuit, and a signal processing circuit. The cardiac signal sensing circuit is configured to sense a plurality of cardiac signals representative of electrical cardiac activity of a subject. The heart sound sensing circuit is configured to sense a plurality of unfiltered heart sound signals representative of intrinsic mechanical cardiac activity of the subject. The signal processing circuit is configured to: detect an R-wave in a sensed cardiac signal and initiate a measurement window in a time relationship to the detected R-wave; determine amplitude of an S1 heart sound using a heart sound signal sensed during the measurement window; trend S1 heart sound amplitudes determined for the plurality of the unfiltered heart sound signals; and generate an alert when the trended S1 heart sound amplitude decreases below a threshold amplitude value.

This section is intended to provide a brief overview of subject matter of the present patent application. It is not intended to provide an exclusive or exhaustive explanation of the invention. The detailed description is included to provide further information about the present patent application such as a discussion of the dependent claims and the interrelation of the dependent and independent claims in addition to the statements made in this section.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

An ambulatory medical device can include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

Devices and methods are described herein for improved assessment of HF of a patient. A fraction of patients with chronic HF may experience an acute HF event such as a HF decompensation event for example. Ambulatory device-based monitoring of HF patients can lead to early detection of any signs and symptoms of HF decompensation, which can lead to early initiation of patient therapy.

Figure 1:
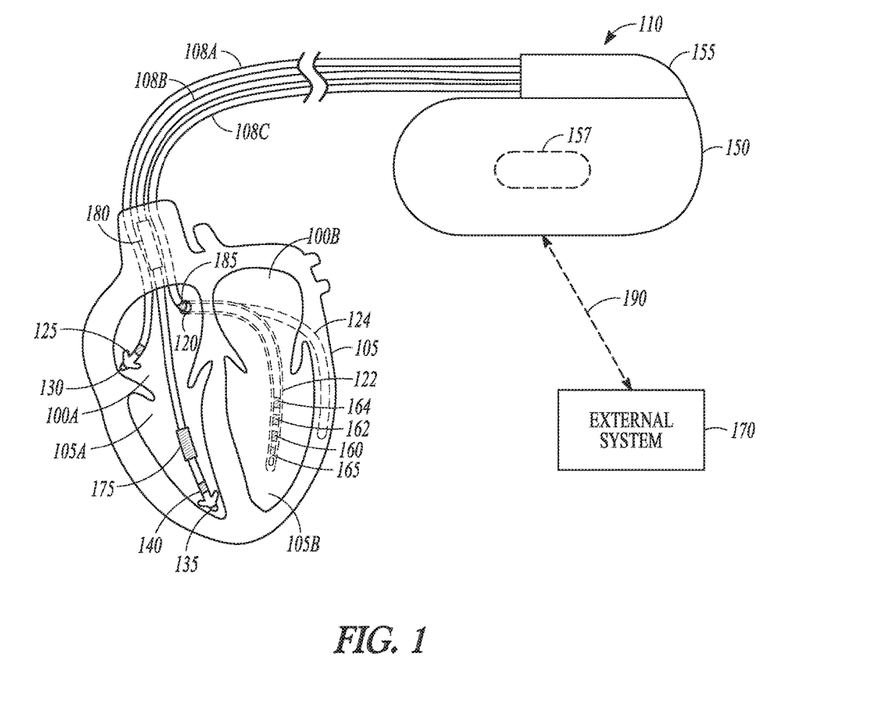
FIG. 1 is an illustration of an example of portions of a medical device system that includes an IMD.

Medical electronic systems can be used to obtain information related to a patient's or subject's physiologic condition. FIG. 1 is an illustration of an example of portions of a system 100 that includes an ambulatory medical device that is an IMD 110. Examples of IMD 110 include, without limitation, a pacemaker, a defibrillator, a cardiac resynchronization therapy (CRT) device, or a combination of such devices. The system 100 also typically includes an IMD programmer or other external device 170 that communicates wireless signals 190 with the IMD 110, such as by using radio frequency (RF) or other telemetry signals.

The IMD 110 can be coupled by one or more leads 108A-C to heart 105. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

Sensed electrical cardiac signals can be sampled to create an electrogram. An electrogram can be analyzed by the IMD and/or can be stored in the IMD and later communicated to an external device where the sampled signals can be displayed for analysis.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between ventricles.

The IMD 110 can include a third cardiac lead 108C attached to the IMD 110 through the header 155. The third cardiac lead 108C includes electrodes 160, 162, 164, and 165 placed in a coronary vein lying epicardially on the left ventricle (LV) 105B via the coronary vein. The third cardiac lead 108C may include anywhere from two to eight electrodes, and may include a ring electrode 185 positioned near the coronary sinus (CS) 120.

Lead 108B can include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150. In some examples, the coil electrodes 175, 180 are used in combination with other electrodes for sensing signals.

Note that although a specific arrangement of leads and electrodes are shown the illustration, an IMD can be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). The present methods and systems will work in a variety of configurations and with a variety of electrodes.

Figure 2:
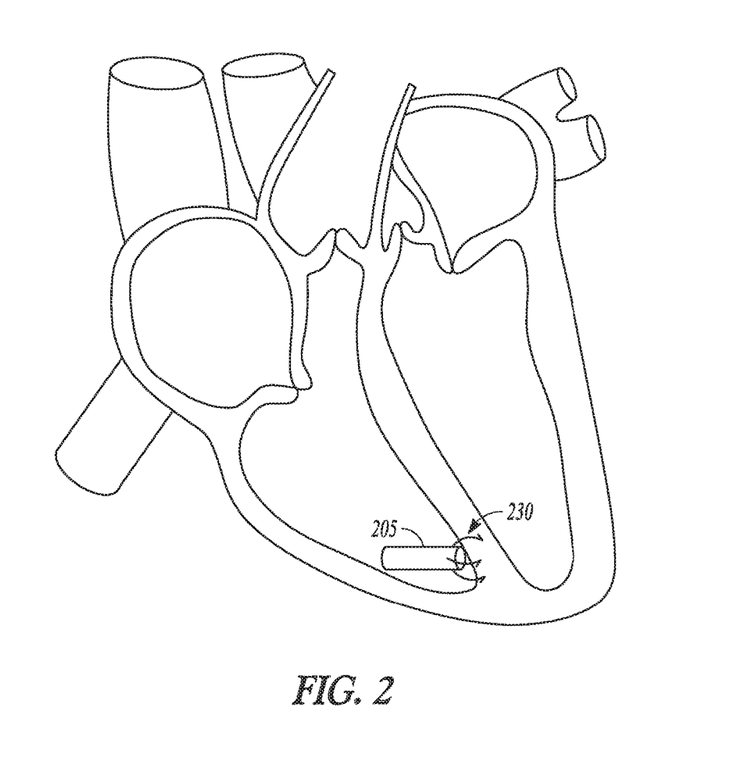
FIG. 2 is an illustration of another example of an IMD.

FIG. 2 is an illustration of an example of an IMD that is leadless. In the example shown, the IMD is a leadless pacemaker 205. The leadless pacemaker 205 is shown positioned at the endocardium within a ventricular chamber, but the leadless pacemaker 205 may be positioned at other locations of the heart. The leadless pacemaker 205 example has a cylindrical or bullet shape housing and may include one or more electrodes arranged along the cylindrical housing to sense electrical signals of the heart and/or provide electrical stimulation for pacing the heart. The one or more electrodes may be used for communication. The leadless pacemaker 205 may include a mechanism 230 to fix the pacemaker to the myocardium. Examples of the fixation mechanism can include one or more tines, one or more barbed tines, and one or more helix-shaped fixation mechanisms. Direct atrial sensing may not be provided by the electrodes for the device placement shown in the example, but the electrodes may provide an RV electrogram signal.

Other examples of an IMD include an implantable loop recorder (ILR), a diagnostic device without leads in the heart, and a neurostimulator (including but not limited to vagus nerve stimulators, baroreceptor stimulators, and spinal cord stimulators), or other IMD.

Figure 3:
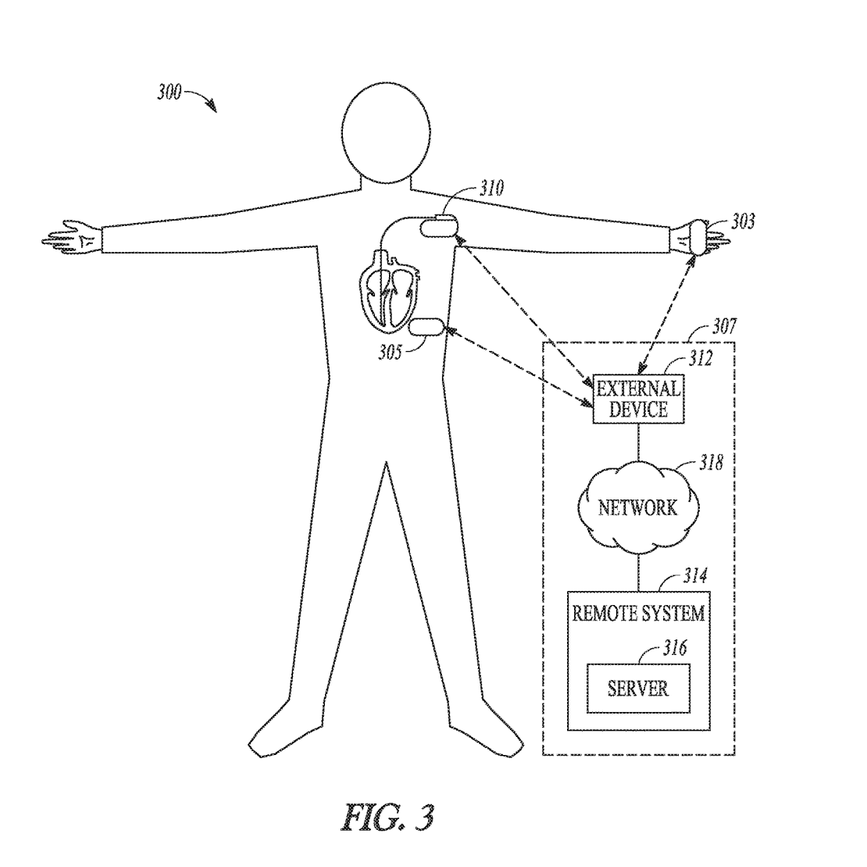
FIG. 3 is an illustration of portions of another example of a medical device system.

FIG. 3 is an illustration of portions of another example of a medical device system 300. The system 300 may include one or more ambulatory medical devices, such as a conventionally implantable or subcutaneously implantable medical device 310, a wearable medical device 305, or a handheld medical device 303. One or more of the medical devices can include a communication circuit (e.g., a telemetry circuit) to communicate the indication of AF to a communication system 307. The communication system 307 can include an external communication device 312 and a remote system 314 that communicates with the external communication device 312 via a network 318 (e.g., the internet, a proprietary computer network, or a cellular phone network). The remote system 314 may include a server 316 remotely located from the external communication device 312 and the subject to perform patient management functions. The external communication device 312 may include a programmer to program therapy parameters of a device-based therapy provided by the implantable medical device. One or both of the external communication device 312 and the remote system 314 may include a display to present physiological information to a user, such as a clinician.

In addition to sensing electrical cardiac signals representative of cardiac electrical activity, an ambulatory medical device can include one or more sensors to sense electrical signals representative of other aspects of a patient's physiology. For instance, an ambulatory medical device may include a heart sound sensing circuit (e.g., the IMD of FIG. 1 may include heart sound sensing circuit 157). Examples of a heart sound sensing circuit include an accelerometer and a microphone. In certain examples, the heart sound sensing circuit includes an accelerometer implantable within a ventricle to measure intracardiac accelerations. A heart sound sensing circuit generates an electrical signal representative of one or more heart sounds. Heart sounds are associated with mechanical vibrations from activity of a patient's heart and the flow of blood through the heart. Heart sounds recur with each cardiac cycle and are separated and classified according to the activity associated with the vibration. The first heart sound (S1) is the vibrational sound made by the heart during tensing of the mitral valve. The second heart sound (S2) marks the beginning of diastole. The third heart sound (S3) and fourth heart sound (S4) are related to filling pressures of the left ventricle during diastole.

The S1 heart sound correlates with contractility of the LV. For instance, the amplitude of the S1 heart sound correlates with pressure produced in the LV. LV contractility may change with changing status of HF of a patient. Therefore monitoring the S1 heart sound can serve as a surrogate for monitoring LV contractility and can be used to detect onset of an acute HF event.

Figure 4:
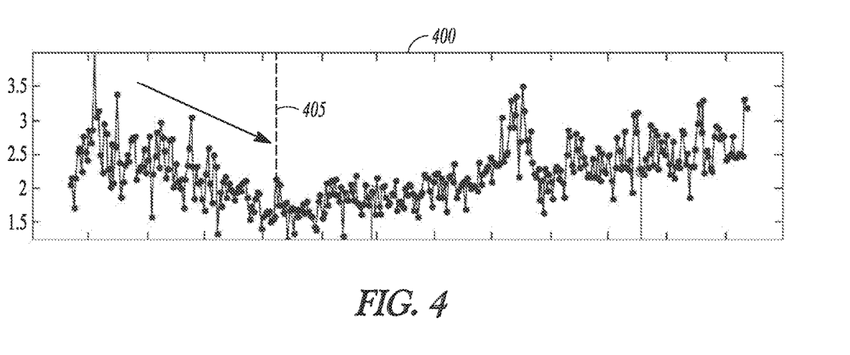
FIG. 4 is a graph showing an example of S1 heart sound amplitude versus time.

FIG. 4 is a graph 400 showing an example of S1 heart sound amplitude versus time for a subject leading up to an acute HF event 405. The vertical axis of the graph is milli-gravity force (mg) sensed with an accelerometer. As indicated by the arrow shown in the graph, the S1 amplitude significantly decreases leading up to the acute HF event 405.

Figure 5:
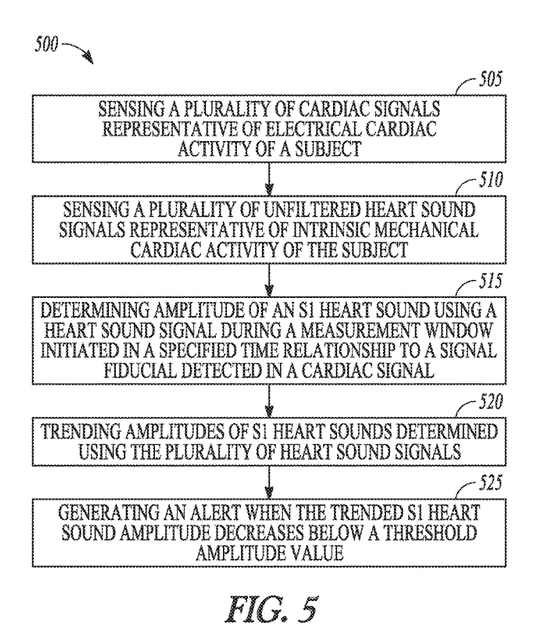
FIG. 5 is a flow diagram of an example of a method of operating a medical device system.

FIG. 5 is a flow diagram of an example of an automated method 500 of operation of a medical device system. At 505, multiple cardiac signals representative of electrical cardiac activity of a subject are sensed and, at 510, a plurality of unfiltered heart sound signals representative of intrinsic mechanical cardiac activity of the subject are sensed. The cardiac signals and the heart sound signals can be sensed using an ambulatory medical device that can be implantable, wearable, or handheld. In certain examples, the cardiac signals are sensed as electrograms. No filtering (e.g., high pass filtering) is used in sensing the heart sound signals to preserve as much information as possible and obtain a full-band heart sound signal.

At 515, the amplitude of an S1 heart sound in the sensed heart sound signals is determined. To locate the S1 heart sound in the signal, the medical device may identify a fiducial in a corresponding cardiac signal, and a heart sound measurement window is initiated in a specified time relationship to the fiducial in the cardiac signal. The medical device system determines the amplitude of the S1 heart sound during the measurement window.

In some examples, the cardiac signal fiducial is an R-wave in the cardiac signal. The R-wave corresponds to the ventricular depolarization portion of the QRS depolarization complex. In certain variations, the medical device includes a peak detector circuit to locate the R-wave in a sensed cardiac signal. In some examples, the cardiac signal fiducial is a Q-wave of a QRS depolarization complex. Initiating the measurement window in a specified time relationship to the cardiac signal fiducial may result in starting the signal analysis during a time in the heart sound signal when the S1 heart sound is likely to occur. Using a measurement window also limits the processing time used by the device to determine S1 amplitudes, which can be useful to extend the battery life of a battery-powered ambulatory medical device.

In other examples, the medical device may identify a fiducial in the heart sound signal to locate the S1 heart sound in the signal. The heart sound measurement window is initiated in a specified time relationship to the fiducial in the heart sound signal. In certain examples, the fiducial is a deflection in the sensed heart sound signal. In certain examples, the fiducial is the largest detected peak in the heart sound signal or the largest peak-to-peak change in the heart sound signal. In certain examples, the fiducial is a deflection detected in a signal generated by filtering the sensed unfiltered heart sound signal.

Figure 6:
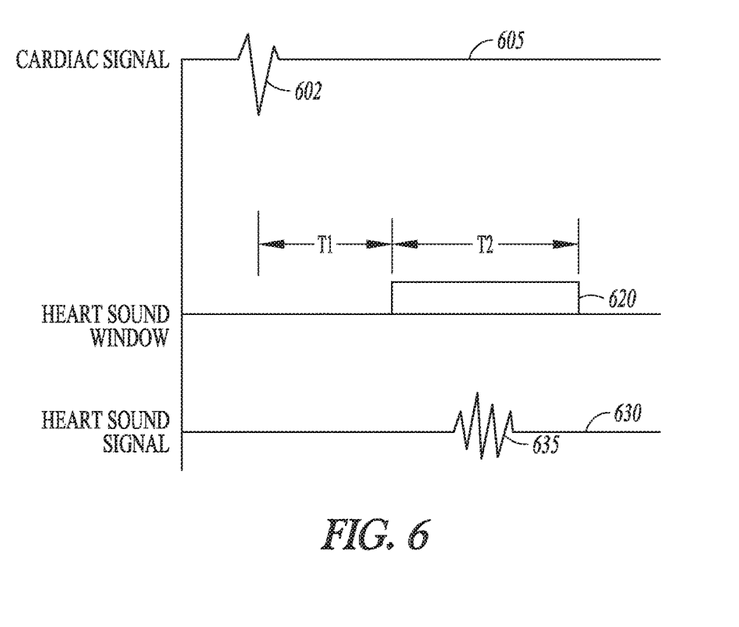
FIG. 6 illustrates an example of initiating a heart sound measurement window.

FIG. 6 illustrates an example of initiating a heart sound measurement window in a time relation to an R-wave. The top waveform 605 illustrates a sensed cardiac signal that includes a QRS complex 602. The large negative peak of the QRS complex 602 corresponds to the R-wave. After time duration T1, a heart sound measurement window 620 is initiated and lasts for time duration T2. The measurement window 620 is shown bracketing the occurrence of the S1 heart sound 635 in heart sound signal 630. The medical system determines the amplitude of the S1 heart sound during the measurement window. In some examples, T1 can be a fixed time duration, such as a number of milliseconds (ms) after an identified R-wave peak. T1 may be a time duration from about 30 ms to about 200 ms. T1 may be chosen according to a patient population or customized for a particular subject.

Returning to the method of FIG. 5 at 520, the amplitude of the S1 heart sounds is trended over time. At 525, the medical device system generates an alert when the trended S1 heart sound amplitude decreases below a threshold amplitude value. The alert may be a signal provided to a process executing on the same medical device or a separate medical device. In some variations, generating the alert includes displaying an alert of risk of an HF event to a user. In some variations, the alert includes storing an indication of risk of an HF event in memory that is later uploaded to a separate medical device.

As shown in the heart sound representation of FIG. 6, the heart sound during the measurement window may include multiple amplitude peaks. According to some examples, the root mean square (RMS) value of the amplitude of the S1 heart sound is determined during the measurement window. The RMS amplitude of S1 heart sound amplitude is trended over time, and the alert is generated when the trended RMS value decreases below a threshold RMS amplitude value.

Figure 7:
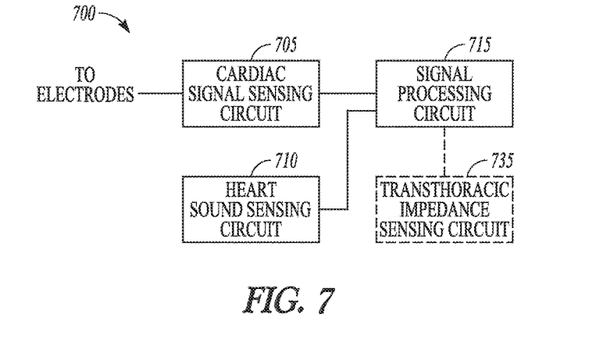
FIG. 7 is a block diagram of an example of a medical device system to detect onset of an acute HF event in a subject.

FIG. 7 is a block diagram of an example of a medical device system to detect onset of an acute HF event in a subject. The system 700 includes a cardiac signal sensing 705, a heart sound sensing circuit 710, and a signal processing circuit 715. The cardiac signal sensing circuit 705 senses cardiac signals representative of electrical cardiac activity of the subject. The heart sound sensing circuit 710 senses heart sound signals representative of intrinsic mechanical cardiac activity of the subject.

The cardiac signal sensing circuit 705 can include sense amplifier circuits and can be electrically coupled to electrodes to detect cardiac signals of the subject. In certain examples, the cardiac signal sensing circuit 705 can be coupled to electrodes that are implantable and the cardiac signal sensing circuit 705 and the heart sound sensing circuit 710 are included in an implantable medical device. In certain variations, the electrodes are implantable in a heart chamber of the subject. In certain variations, the electrodes are subcutaneously implantable. In certain examples, the electrodes are surface electrodes and the cardiac signal sensing circuit 705 and the heart sound sensing circuit 710 are included in a wearable medical device or a handheld medical device.

The heart sound signals produced by the heart sound sensing circuit 710 are not filtered when they are analyzed. The unfiltered electrical signals produced by the heart sound sensing circuit 710 are sometimes referred to as "raw" signals. The unfiltered heart sound signals are full band signals and may include more information than heart sound signals that are filtered, such as to remove lower frequency components of the heart sound signal for instance.

The signal processing circuit 715 can include can include a microprocessor, a digital signal processor, application specific integrated circuit (ASIC), or other type of processor, interpreting or executing instructions included in software or firmware. The signal processing circuit 715 can include other sub-circuits. The signal processing circuit 715 and the sub-circuits may include software, hardware, firmware or any combination thereof. One or both of the signal processing circuit and the sub-circuits may configured through the software, hardware, firmware or the combinations to perform the functions described Multiple functions can be performed in one or more of the circuits as desired.

In some examples, the signal processing circuit 715 is included in the same ambulatory medical device as the cardiac signal sensing circuit 705 and the heart sound sensing circuit 710. The signal processing circuit 715 detects the R-wave in a sensed cardiac signal and initiates the heart sound measurement window in a time relationship to the detected R-wave. The signal processing circuit 715 determines the amplitude of the S1 heart sound using a heart sound signal sensed during the measurement window.

Figure 8:
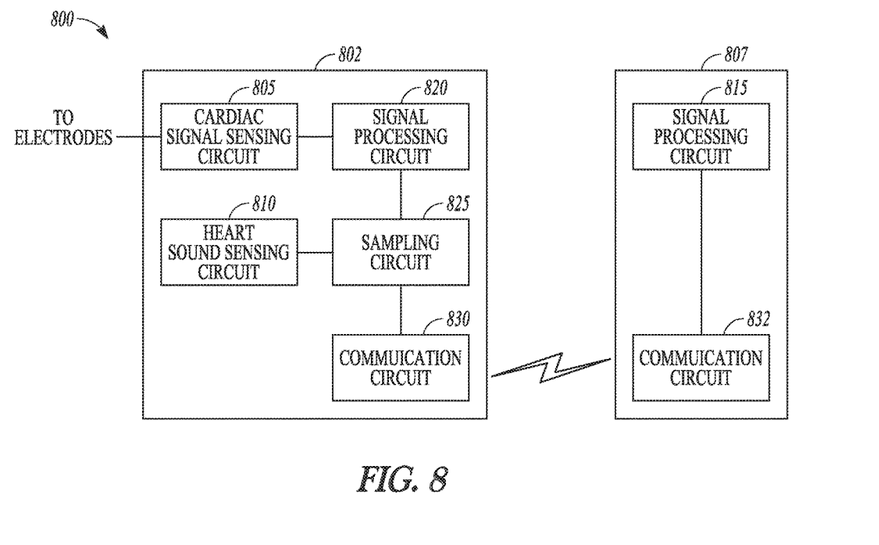
FIG. 8 is a block diagram of another example of a medical device system to detect onset of an acute HF event in a subject.

FIG. 8 is a block diagram of another example of a medical device system. The system 800 includes a first ambulatory medical device 802 and a second medical device 807. The ambulatory medical device 802 includes the cardiac signal sensing 805 and the heart sound sensing circuit 810 to produce the cardiac signals and the heart signals. The ambulatory medical device 802 also includes an R-wave detection circuit 820 that detects the R-wave in a sensed cardiac signal. The ambulatory medical device 802 also includes a sampling circuit 825. The sampling circuit 825 initiates a measurement window in a time relation to an R-wave detected in a cardiac signal. During the measurement window, the sampling circuit 825 produces sampled values of the heart sound signal. In some variations, the sampling circuit 825 includes an analog to digital (ADC) circuit to produce the sampled values. The sampled values of the heart sound signal include sampled values for the S1 heart sound because of the position and duration of the measurement window.

The ambulatory medical device 802 includes a communication circuit 830 that communicates the sampled values of the heart sound signal to the second medical device 807. The second medical device 807 may be another ambulatory medical device, a remote server, or a medical device programmer. The second medical device 807 includes a second communication circuit 832 that communicates information with the ambulatory medical device 802 including to receive the sampled values of the heart sound signal. The second medical device 807 includes the signal processing circuit 815 which determines the amplitude of an S1 heart sound using the sampled values of the heart sound signal collected during the measurement window.

Returning to FIG. 7, the signal processing circuit 715 trends S1 heart sound amplitudes determined for multiple heart sound signals. Values of the amplitude are trended for a specified (e.g., programmed) duration of time. The signal processing circuit 715 generates an alert when the trended S1 heart sound amplitude decreases below a threshold amplitude value. The alert can be a signal communicated to a different process executing on the signal processing circuit 715. The alert can be a value stored in memory of an ambulatory medical device that is later uploaded to a second device. In the system of the example of FIG. 8, the second medical device 807 may provide the alert to a user. The second medical device 807 can include a display to present the alert to the user, or communicate the alert to a separate device to present the alert. The alert presented to the user may indicate that there is increased risk of the subject experiencing an HF event.

The alert can be used by the system to adjust device-based therapy. For example, an alert of a change in status of heart failure can initiate a change to cardiac resynchronization therapy (CRT). The adjustment may include a change to one or more of pacing pulse amplitude, a change to delay between pacing heart chambers such as an interventricular pace delay. In some examples, the change may be to change one or more electrodes used to deliver CRT, thereby changing the vector used to deliver CRT. In some examples, the alert can initiate a recommendation to change titration of a drug therapy for the patient.

Returning to FIG. 7, in some examples the signal processing circuit 715 determines the RMS value of the amplitude of the S1 heart sound over the measurement window. The RMS amplitude is trended over time, and the alert is generated when the trended RMS amplitude of S1 heart sounds decreases below a threshold amplitude value.

In some examples, the signal processing circuit 715 calculates at least one of peak amplitude values during the measurement window, peak-to-peak (PP) amplitude values during the measurement window, or energy measurement values representative of intrinsic mechanical cardiac activity during at least a portion of the measurement window. The signal processing circuit 715 trends one or more of the peak amplitude values, PP amplitude values, and energy measurement values, and generates the alert when the trended peak amplitude values, PP amplitude values, and energy measurement values decrease below a specified threshold peak amplitude value, PP amplitude value, or energy measurement value.

In some examples, the signal processing circuit 715 calculates a daily central tendency of the S1 heart sound amplitudes over a time duration of M hours; M being a positive integer less than or equal to twenty-four. Some examples of a central tendency include a calculated average, mean, or median value of the S1 amplitude. In certain examples, the daily central tendency is a central tendency of RMS values of S1 heart sound amplitude. The signal processing circuit 715 trends the daily central tendency over multiple days and generates the alert when the trended daily central tendency satisfies a threshold daily central tendency value.

In some examples, the signal processing circuit 715 calculates a short-term central tendency and a long-term central tendency of the S1 heart sound amplitude. In certain examples, the signal processing circuit 715 calculates a short-term central tendency and a long-term central tendency of the RMS value of the S1 heart sound amplitude. The long-term central tendency can be viewed as a baseline for the S1 amplitude. The difference between the short-term central tendency and the long-term central tendency can be used to detect that the subject is at risk of experiencing an acute HF event.

The short-term central tendency may be calculated over a time duration of N days; N being a positive integer (e.g., $N \leq 14$). The long-term central tendency of the S1 amplitude is calculated for a time duration longer than N days. In an example intended to be illustrative and non-limiting, the short-term central tendency is calculated over three days and the long-term central tendency is calculated over forty days. The long-term central tendency may be calculated at least partially prior to the short-term central tendency.

In certain examples, the short-term central tendency is calculated during different days than the long-term central tendency. In an illustrative example, a day is scheduled in the medical device system to measure the S1 amplitude. The long-term central tendency may be calculated over a time duration of 40 days beginning 59 days prior to the scheduled measurement day. The short-term central tendency is calculated over a time duration of three days starting two days before the scheduled measurement day.

As explained previously, the difference between the short-term central tendency and the long-term central tendency can be used to detect that the subject is at risk of experiencing an acute HF event. In some examples, the signal processing circuit 715 trends a long-term to short-term difference between the calculated long-term central tendency and the calculated short-term central tendency of the S1 heart sound amplitude. The signal processing circuit 715 may generate the alert when the trend of the short-term central tendency of the S1 heart sound amplitude is decreasing and a trend of the long-term to short-term difference exceeds a threshold difference value.

Figure 9:
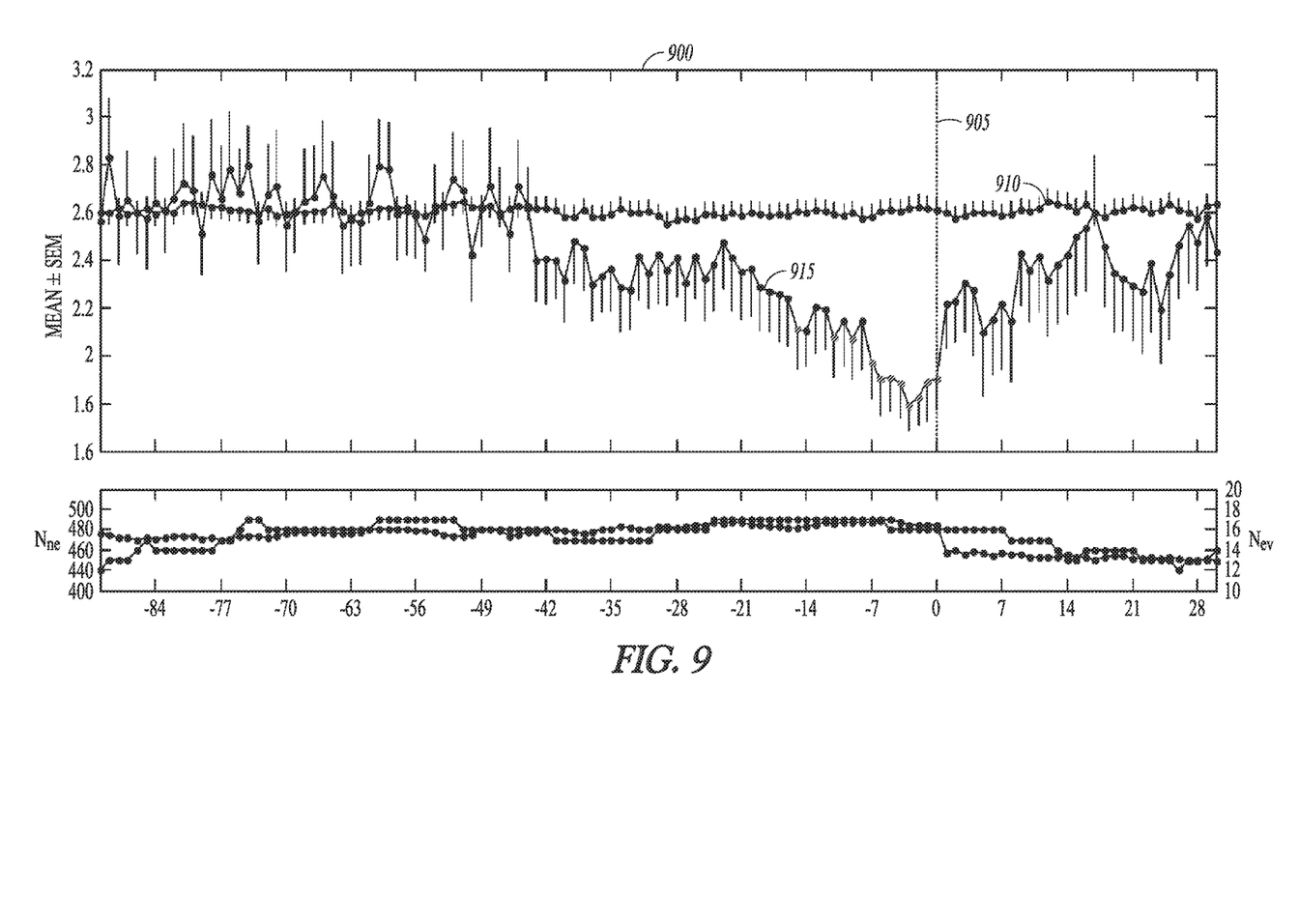
FIG. 9 is a graph showing an example of averaged S1 heart sound amplitude versus time.

FIG. 9 is a graph 900 that shows an example of S1 amplitude. The graph shows values of a long-term average 910 and a short-term average 915. The graph shows that the difference between the short-term average and the long-term average (or baseline) increases leading up to the reference acute HF event 905.

Returning to FIG. 7, in certain examples the signal processing circuit 715 trends the value of a ratio that includes the long-term to short-term difference and the calculated long-term central tendency of the S1 heart sound (e.g., ratio=(|long-term to short-term difference|)/long-term central tendency), and generates the alert when the ratio satisfies a threshold ratio value. In certain examples, the signal processing circuit 715 trends the percentage of the long-term to short-term difference to the calculated long-term central tendency of the S1 amplitude, and generates the alert when the percentage satisfies a threshold ratio value.

In some examples, the signal processing circuit 715 smooths the determined values of the long-term to short-term difference using a smoothing function, and generates the alert when the short-term central tendency of the S1 heart sound is decreasing and the smoothed value of the long-term to short-term difference exceeds the threshold difference value.

To smooth the values of the long-term to short-term difference in S1 amplitude, the difference values calculated over time may be weighted and then combined. The weights can be determined according to the smoothing function. In certain examples, the signal processing circuit 715 smooths values of the long-term to short-term difference using an exponential smoothing function.

Figure 10:
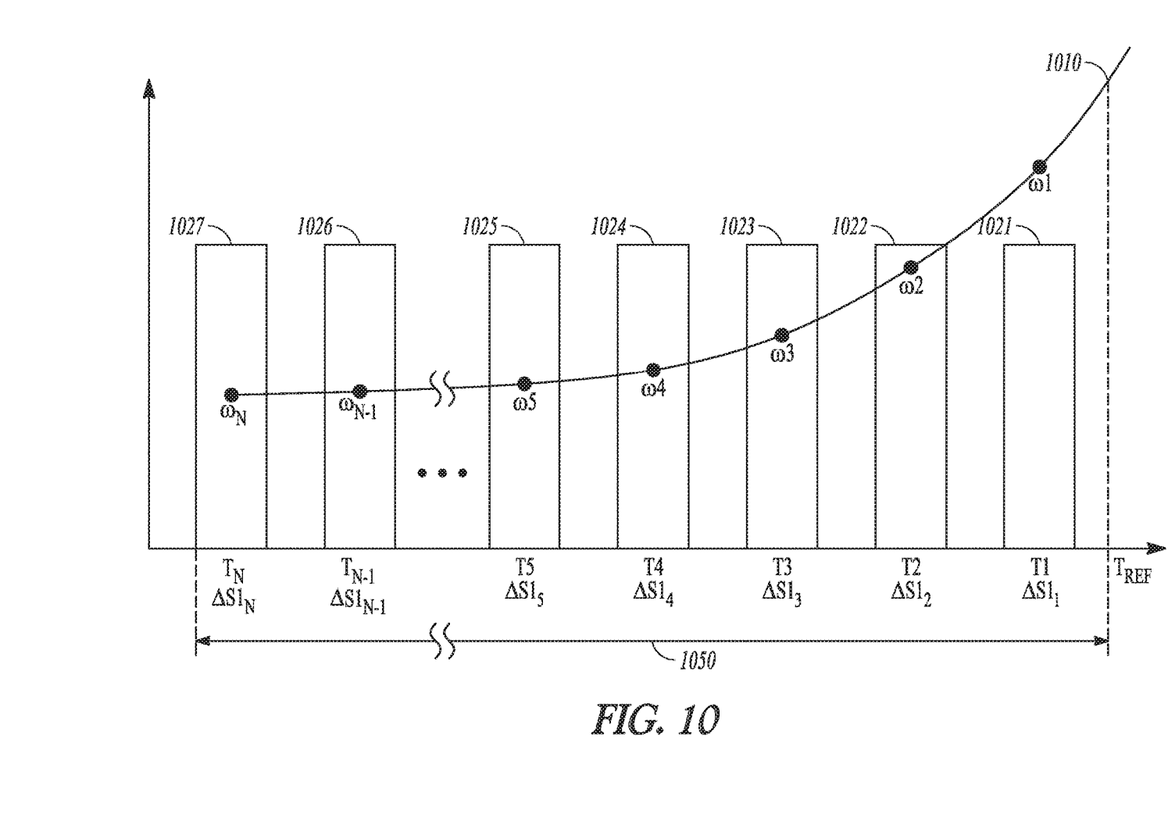
FIG. 10 illustrates an example of using a smoothing function to smooth the values of the determined long-term to short-term differences in S1 heart sound amplitude.

FIG. 10 shows an example of using a smoothing function to smooth the values of the determined long-term to short-term differences in S1 amplitude. The reference time ($T_{ref}$) corresponds to the time of the scheduled measurement. Timing windows 1021-1027 represent the measurement windows $T_1$-$T_N$ used to calculate the short-term central tendency of the S1 amplitude. Depending on the short-term calculation timing, the measurement windows may be contiguous or have a gap between them as shown in the example of FIG. 10. The waveform 1010 corresponds to the smoothing function and determines the weights ($\omega_1$-$\omega_N$) used in the smoothing. The signal processing circuit 715 uses the weights to modify (e.g., through multiplication) the calculated long-term to short-term differences $\Delta S1_1$ through $\Delta S1_N$. Determined values of the difference can be smoothed for a duration of a smoothing window 1050 (e.g., 30 days).

In the example of FIG. 10, the smoothing function is an exponential smoothing function, and the weights are calculated as weight $\omega_i$ can be computed as $\omega_i = A \cdot \exp[-k(|T_{Ref} - T_i|)]$. The time $T_i$ used in the calculating the weight may be the time at the center of the measurement window. The long-term to short-term differences calculated with measurement windows farther away in time from $T_{Ref}$ may be weighted less than the differences calculated with measurement windows closer in time to $T_{Ref}$. For example, the weight factor for $\Delta S1_1$, $\omega_1 = A \cdot \exp[-k(T_{Ref} - T_1)]$, is greater than the weight factor for $\Delta S1_2$, $\omega_2 = A \cdot \exp[-k(T_{Ref} - T_2)]$.

The smoothed long-term to short-term difference value ($\Delta S1$) may be the weighted accumulation of the differences of the weighted differences of the measurement windows (e.g., $\Delta S1 = \Sigma_{i=1}^{N} = \omega_i \cdot \Delta S1_i$). The signal processing circuit 715 compares the smoothed difference value to the threshold difference value to detect the risk of an acute HF event. The smoothed difference may preserve local changes of the long-term to short-term difference in the determined trend. Other smoothing functions can be used for the smoothing such as a logistic decay function, a logarithm decay function, or a linear or a piece-wise linear decay function.

Returning to FIG. 7, the signal processing circuit 715 may combine trending of the S1 amplitude with indications from other sensor outputs to detect the risk of an acute HF event. In some examples, the signal processing circuit 715 determines amplitudes of S3 heart sounds using the heart sound signals. The signal processing circuit 715 may initiate a different measurement window to determine the S3 amplitude. In certain examples, the signal processing circuit 715 calculates the RMS value of the S3 amplitude. The signal processing circuit 715 may generate the alert when the trended the S1 heart sound amplitudes decrease below a threshold amplitude value and the amplitude of the S3 heart sound exceeds an S3 amplitude threshold value.

The trend of the S1 amplitude can be combined with indications from other sensing circuits to detect the risk of an acute HF event. A worsening condition of HF may be accompanied by increased heart rate. In some examples, the signal processing circuit 715 determines heart rate of the subject using the plurality of cardiac signals sensed by the cardiac signal sensing circuit 705. The signal processing circuit 715 may generate the alert when the trended S1 heart sound amplitudes decrease below a threshold amplitude and the determined heart rate of the subject increases above a threshold heart rate value.

According to some examples, the system 700 includes a thoracic impedance sensing circuit 735 that generates a thoracic impedance signal representative of thoracic impedance of the subject. To measure impedance of cardiac or thoracic tissue, thoracic impedance sensing circuit 735 provides current between cardiac electrodes and measures the resulting voltage using the same of different electrodes. The impedance can be determined by the medical device using Ohm's Law (R=V/I). For example, in FIG. 1 impedance can be measured between coil electrode 175 and an electrode formed on the IMD can 150. This can provide a measure of the impedance across the thorax region of the subject, which is sometimes called intra-thoracic total impedance (ITTI). An approach to measuring thoracic impedance is described in Hartley et al., U.S. Pat. No. 6,076,015 "Rate Adaptive Cardiac Rhythm Management Device Using Transthoracic Impedance," filed Feb. 27, 1998, which is incorporated herein by reference.

In some examples, the signal processing circuit 715 determines a value of intra-thoracic total impedance (ITTI) of the subject using the thoracic impedance signal. A worsening condition of HF may include increased fluid accumulation in the lungs. As the fluid accumulates, the increased fluid may cause the impedance of current pathways through the lungs to be reduced. This in turn causes the amplitude of a sensed thoracic impedance signal to be reduced for a given respiration level. The signal processing circuit 715 may generate the alert when the trended S1 heart sound amplitudes decrease below a threshold amplitude value and the value of ITTI decreases below a threshold ITTI value.

The sensed thoracic impedance signal can be modulated by respiration of the subject, and the sensed impedance signal can be used to monitor respiration of the subject. A worsening condition of HF may include more rapid and shallower breathing by the subject. In certain examples, the signal processing circuit 715 determines a value of respiration rate using the thoracic impedance signal, and generate the alert when the trended S1 heart sound amplitudes decrease below a threshold amplitude and the value of respiration rate increases above a threshold respiration rate value. In certain examples, the signal processing circuit 715 also determines a value of tidal volume (TV) of the subject using the thoracic impedance signal. The signal processing circuit 715 generates the alert when the trended S1 heart sound amplitudes decrease below a threshold amplitude and the TV decreases below a specified threshold TV value. In certain examples, the signal processing circuit 715 generates the alert when the trended S1 heart sound amplitudes decrease below a threshold amplitude and a ratio that includes the respiration rate (RR) and the TV (e.g., RR/TV=rapid shallow breathing index, or RSBI) satisfies a threshold ratio value.

The devices, systems, and methods described herein provide device-based detection of a pattern of decreasing amplitude in the S1 heart sound. Detection of the decreasing pattern can be used to generate an alert of early detection of any signs and symptoms of HF decompensation, which can lead to early initiation of patient therapy, such as treating the patient with a diuretic drug or changing the titration of a diuretic drug for example.

ADDITIONAL DESCRIPTION AND EXAMPLES

Example 1 includes subject matter (such as an apparatus) comprising a cardiac signal sensing circuit configured to sense a plurality of cardiac signals representative of electrical cardiac activity of a subject; a heart sound sensing circuit configured to sense a plurality of unfiltered heart sound signals representative of intrinsic mechanical cardiac activity of the subject; and a signal processing circuit configured to: detect a signal fiducial in a sensed cardiac signal and initiate a measurement window in a time relationship to the detected fiducial; determine amplitudes of S1 heart sounds during the measurement window using the plurality of sensed unfiltered heart sound signals; trend S1 heart sound amplitudes determined for the plurality of the unfiltered heart sound signals; and generate an alert when the trended S1 heart sound amplitude decreases below a threshold amplitude value.

In Example 2, the subject matter of Example 1 optionally includes a signal processing circuit configured to: calculate a short-term central tendency of the S1 heart sound amplitudes over a time duration of N days, where N is a positive integer less than or equal to five; calculate a long-term central tendency of the S1 heart sound amplitudes for a time duration longer than N days, wherein the long-term central tendency is calculated during different days than the short-term central tendency and is calculated at least partially prior to the short-term central tendency; trend a long-term to short-term difference between the calculated long-term central tendency of the S1 heart sound amplitudes and the calculated short-term central tendency of the S1 heart sound amplitudes; and generate the alert when a trend of the short-term central tendency of the S1 heart sound amplitudes is decreasing and a trend of the long-term to short-term difference exceeds a threshold difference value.

In Example 3, the subject matter of Example 2 optionally includes a signal processing circuit configured to: trend a value of a ratio that includes the long-term to short-term difference and the calculated long-term central tendency of the S1 heart sound; and generate the alert when the ratio satisfies a threshold ratio value.

In Example 4, the subject matter of any one or more of Examples 2-3 optionally includes a signal processing circuit configured to: smooth values of the long-term to short-term difference using a smoothing function; and generate the alert when the short-term central tendency of the S1 heart sound is decreasing and the smoothed value of the long-term to short-term difference exceeds the threshold difference value.

In Example 5, the subject matter of Example 4 optionally includes a signal processing circuit configured to smooth values of the long-term to short-term difference using an exponential smoothing function.

In Example 6, the subject matter of any one or more of Examples 1-5 optionally includes a signal processing circuit configured to: calculate a root mean square (RMS) value of the S1 heart sound amplitude during the measurement window; trend RMS values of the S1 heart sound amplitude using the heart sound signals, and generate the alert when the trended RMS values of the S1 heart sound amplitude decrease below a threshold RMS amplitude value.

In Example 7, the subject matter of any one or more of Examples 1-6 optionally includes a signal processing circuit configured to detect an R-wave in the sensed cardiac signal and initiate a measurement window in a time relationship to the R-wave.

In Example 8, the subject matter of any one or more of Examples 1-7 optionally includes a signal processing circuit configured to: calculate at least one of peak amplitude values during the measurement window, peak-to-peak (PP) amplitude values during the measurement window, and energy measurement values representative of intrinsic mechanical cardiac activity during at least a portion of the measurement window; trend the at least one of the peak amplitude values, PP amplitude values, and energy measurement values; and generate the alert when the trended at least one of the peak amplitude values, PP amplitude values, and energy measurement values decrease below a threshold value.

In Example 9, the subject matter of any one or more of Examples 1-8 optionally includes a signal processing circuit configured to: calculate a daily central tendency of the S1 heart sound amplitudes over a time duration of M hours, wherein M is a positive integer less than or equal to twenty-four; trend the daily central tendency over multiple days; and generate the alert when the daily central tendency satisfies a threshold daily central tendency value.

In Example 10, the subject matter of any one or more of Examples 1-9 optionally includes a signal processing circuit configured to: determine amplitudes of S3 heart sounds using the heart sound signals; and generate the alert when the trended the S1 heart sound amplitudes decrease below a threshold amplitude value and the amplitude of the S3 heart sound exceeds an S3 amplitude threshold value.

In Example 11, the subject matter of any one or more of Examples 1-10 optionally includes a thoracic impedance sensing circuit configured to generate a thoracic impedance signal representative of thoracic impedance of the subject, and a signal processing circuit optionally configured to determine at least one of: a value of intra-thoracic total impedance (ITTI) of the subject using the thoracic impedance signal, and generate the alert when the trended S1 heart sound amplitudes decrease below a threshold amplitude value and the value of ITTI decreases below a threshold ITTI value; a value of respiration rate using the thoracic impedance signal, and generate the alert when the trended S1 heart sound amplitudes decrease below a threshold amplitude and the value of respiration rate increases above a threshold respiration rate value; a value of tidal volume (TV) of the subject using the thoracic impedance signal, and generate the alert when the trended S1 heart sound amplitudes decrease below a threshold amplitude and the TV decreases below a specified threshold TV value; or a value of respiration rate of the subject and a value of TV of the subject using the thoracic impedance signal, and generate the alert when the trended S1 heart sound amplitudes decrease below a threshold amplitude and a ratio including respiration rate and TV satisfies a threshold ratio value.

In Example 12, the subject matter of any one or more of Examples 1-11 optionally includes a signal processing circuit is configured to determine heart rate of the subject using the plurality of cardiac signals, and generate the alert when the trended S1 heart sound amplitudes decrease below a threshold amplitude and the determined heart rate of the subject increases above a threshold heart rate value.

Example 13 includes subject matter (such as a method of operating an ambulatory medical device, a means for performing acts, or a machine-readable medium including instructions that, when performed by the machine, cause the machine to perform acts), or can optionally be combined with the subject matter of one or any combination of Examples 1-12 to include such subject matter, comprising sensing a plurality of cardiac signals representative of electrical cardiac activity of a subject; sensing a plurality of unfiltered heart sound signals representative of intrinsic mechanical cardiac activity of the subject; determining amplitude of an S1 heart sound using a heart sound signal during a measurement window initiated in a specified time relationship to a signal fiducial detected in a cardiac signal; trending amplitudes of S1 heart sounds determined using the plurality of unfiltered heart sound signals; and generating an alert when the trended S1 heart sound amplitude decreases below a threshold amplitude value.

In Example 14, the subject matter of Example 13 optionally includes: calculating a short-term central tendency of the amplitudes of S1 heart sounds for a time duration of N days, wherein N is a positive integer less than or equal to five; calculating a long-term central tendency of the amplitudes of S1 heart sounds for a time duration longer than N days, wherein the long-term central tendency is calculated during different days than the short-term central tendency and is calculated at least partially prior to the short-term central tendency; trending a long-term to short-term difference between the calculated long-term central tendency of the S1 heart sound amplitudes and the calculated short-term central tendency of the S1 heart sound amplitudes; and generating the alert when a trend of the short-term central tendency of the S1 heart sound amplitudes is decreasing and a trend of the long-term to short-term difference exceeds a threshold difference value.

In Example 15, the subject matter of Example 14 optionally includes smoothing values of the long-term to short-term difference using an exponential smoothing function, and wherein the generating an alert includes generating the alert when the short-term central tendency of the S1 heart sound is decreasing and the smoothed value of the long-term to short-term difference exceeds the threshold difference value.

In Example 16, the subject matter of any one or more of Examples 13-15 optionally includes: calculating a daily central tendency of the amplitudes of S1 heart sounds over a time duration of M hours, wherein M is a positive integer less than or equal to twenty-four; trending the daily central tendency over multiple days; and generating the alert when the daily central tendency satisfies a threshold daily central tendency value.

Example 17 includes subject matter (such as a system), or can optionally be combined with the subject matter of one or any combination of Examples 1-16 to include such subject matter, comprising a first medical device and a second medical device, wherein the first medical device includes: a cardiac signal sensing circuit configured to sense a cardiac signal representative of electrical cardiac activity of a subject; an R-wave detection circuit configured to detect an R-wave in a sensed cardiac signal; a heart sound sensing circuit configured to sense an unfiltered heart sound signal representative of intrinsic mechanical cardiac activity of the subject; a sampling circuit configured to produce sampled values of the unfiltered heart sound signal during a measurement window initiated in a time relation to the R-wave detected in the cardiac signal; a first communication circuit configured to communicate the sampled values to the second medical device, wherein the second medical device includes: a second communication circuit configured to communicate information with the first medical device including to receive the sampled values; and a signal processing circuit configured to: calculate a root mean square value of amplitude of an S1 heart sound during the measurement window; trend RMS values of S1 heart sound amplitude calculated for a plurality of unfiltered heart sound signals; and generate an alert when the trended RMS values of S1 heart sound amplitude decreases below a threshold amplitude value.

In Example 18, the subject matter of Example 17 optionally includes a signal processing circuit of the second medical device is configured to: calculate a short-term central tendency of the RMS values of S1 heart sound amplitude for a time duration of N days, where N is a positive integer less than or equal to five; calculate a long-term central tendency of the RMS values of S1 heart sound amplitude for a time duration longer than N days, wherein the long-term central tendency is calculated during different days than the short-term central tendency and is calculated at least partially prior to the short-term central tendency; trend a long-term to short-term difference between the calculated long-term central tendency and the calculated short-term central tendency; and generate the alert when a trend of the short-term central tendency is decreasing and a trend of the long-term to short-term difference exceeds a threshold difference value.

In Example 19, the subject matter of any one or more of Examples 17-18 optionally includes the first medical device being a wearable or handheld medical device and the second medical device including a server.

In Example 20, the subject matter of any one or more of Examples 17-19 optionally includes the first medical device being an implantable medical device and the second medical device including a programmer for the implantable medical device.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
    a cardiac signal sensing circuit configured to sense a plurality of cardiac signals representative of electrical cardiac activity of a subject;
    a heart sound sensing circuit configured to sense a plurality of heart sound signals representative of intrinsic mechanical cardiac activity of the subject; and
    a signal processing circuit configured to:
    detect a signal fiducial in a sensed cardiac signal and initiate a measurement window in a time relationship to the detected fiducial;
    determine amplitudes of S1 heart sounds during the measurement window using the plurality of sensed heart sound signals;
    calculate a short-term central tendency of the S1 heart sound amplitudes over a time duration of N days, where N is a positive integer less than or equal to five:
    calculate a long-term central tendency of the S1 heart sound amplitudes for a time duration longer than N days, during different days than the short-term central tendency, and at least partially prior to the short-term central tendency;
    trend a long-term to short-term difference between the calculated long-term central tendency of the S1 heart sound amplitudes and the calculated short-term central tendency of the S1 heart sound amplitudes; and
    generate an alert using the calculated short-term central tendency and the calculated long-term central tendency.

2. The apparatus of claim 1, wherein the signal processing circuit is configured to: trend a value of a ratio that includes the long-term to short-term difference and the calculated long-term central tendency of the S1 heart sound; and generate the alert when the ratio satisfies a threshold ratio value.

3. The apparatus of claim 1, wherein the signal processing circuit is configured to: smooth values of the long-term to short-term difference using a smoothing function; and generate the alert when the short-term central tendency of the S1 heart sound is decreasing and the smoothed value of the long-term to short-term difference exceeds the threshold difference value.

4. The apparatus of claim 3, wherein the signal processing circuit is configured to smooth values of the long-term to short-term difference using an exponential smoothing function.

5. The apparatus of claim 1, wherein the signal processing circuit is configured to:
calculate a root mean square (RMS) value of the S1 heart sound amplitude during the measurement window;
and use RMS values of the S1 heart sound amplitude to calculate the short-term central tendency and the long-term central tendency of the S1 heart sound amplitudes.

6. The apparatus of claim 1, wherein the signal processing circuit is configured to detect an R-wave in the sensed cardiac signal and initiate a measurement window in a time relationship to the R-wave.

7. The apparatus of claim 1, wherein the signal processing circuit is configured to:
calculate at least one of peak amplitude values during the measurement window, peak-to-peak (PP) amplitude values during the measurement window, and energy measurement values representative of intrinsic mechanical cardiac activity during at least a portion of the measurement window;
calculate the short-term central tendency and the long-term central tendency of the S1 heart sound amplitudes using the at least one of the peak amplitude values, PP amplitude values, and energy measurement values.

8. The apparatus of claim 1, wherein the signal processing circuit is configured to:
trend a long-term to short-term difference between the calculated long-term central tendency of the S1 heart sound amplitudes and the calculated short-term central tendency of the S1 heart sound amplitudes, and
generate the alert when a trend of the calculated short-term central tendency of the S1 heart sound amplitudes is decreasing and a trend of the long-term to short-term difference exceeds a threshold difference value.

9. The apparatus of claim 1, wherein the signal processing circuit is configured to: determine amplitudes of S3 heart sounds using the heart sound signals; and generate the alert when a trend of the long-term to short-term difference exceeds a threshold difference value and the amplitude of the S3 heart sound exceeds an S3 amplitude threshold value.

10. The apparatus of claim 1, including a thoracic impedance sensing circuit configured to generate a thoracic impedance signal representative of thoracic impedance of the subject, wherein the signal processing circuit is configured to determine at least one of:
a value of intra-thoracic total impedance (ITTI) of the subject using the thoracic impedance signal, and generate the alert when a trend of the long-term to short-term difference exceeds a threshold difference value and the value of ITTI decreases below a threshold ITTI value;
a value of respiration rate using the thoracic impedance signal, and generate the alert when a trend of the long-term to short-term difference exceeds a threshold difference value and the value of respiration rate increases above a threshold respiration rate value;
a value of tidal volume (TV) of the subject using the thoracic impedance signal, and generate the alert when a trend of the long-term to short-term difference exceeds a threshold difference value and the TV decreases below a specified threshold TV value; or
a value of respiration rate of the subject and a value of TV of the subject using the thoracic impedance signal, and generate the alert when a trend of the long-term to short-term difference exceeds a threshold difference value and a ratio including respiration rate and TV satisfies a threshold ratio value.

11. The apparatus of claim 1, wherein the signal processing circuit is configured to determine heart rate of the subject using the plurality of cardiac signals, and generate the alert when a trend of the long-term to short-term difference exceeds a threshold difference value and the determined heart rate of the subject increases above a threshold heart rate value.

12. A method of controlling operation of a medical device system, the method comprising:
sensing a plurality of cardiac signals representative of electrical cardiac activity of a subject;
sensing a plurality of heart sound signals representative of intrinsic mechanical cardiac activity of the subject;
determining amplitude of an S1 heart sound using a heart sound signal during a measurement window initiated in a specified time relationship to a signal fiducial detected in a cardiac signal;
calculating a short-term central tendency of the S1 heart sound amplitudes over a time duration of N days, where N is a positive integer less than or equal to five;
calculating a long-term central tendency of the S1 heart sound amplitudes for a time duration longer than N days, during different days than the short-term central tendency, and at least partially prior to the short-term central tendency;
trending a long-term to short-term difference between the calculated long-term central tendency of the S1 heart sound amplitudes and the calculated short-term central tendency of the S1 heart sound amplitudes; and
generating an alert using the calculated short-term central tendency and long-term central tendency.

13. The method of claim 12, wherein the trending a long-term to short-term difference includes smoothing values of the long-term to short-term difference using an exponential smoothing function, and wherein the generating an alert includes generating the alert when the short-term central tendency of the S1 heart sound is decreasing and the smoothed value of the long-term to short-term difference exceeds the threshold difference value.

14. The method of claim 12, wherein the trending amplitudes of S1 heart sounds includes:
trending a long-term to short-term difference between the calculated long-term central tendency of the S1 heart sound amplitudes and the calculated short-term central tendency of the S1 heart sound amplitudes; and
generating the alert when a trend of the calculated short-term central tendency of the S1 heart sound amplitudes is decreasing and a trend of the long-term to short-term difference exceeds a threshold difference value.

15. A system comprising a first medical device and a second medical device, wherein the first medical device includes:

a cardiac signal sensing circuit configured to sense a cardiac signal representative of electrical cardiac activity of a subject;

an R-wave detection circuit configured to detect an R-wave in a sensed cardiac signal;

a heart sound sensing circuit configured to sense an heart sound signal representative of intrinsic mechanical cardiac activity of the subject;

a sampling circuit configured to produce sampled values of the heart sound signal during a measurement window initiated in a time relation to the R-wave detected in the cardiac signal;

a first communication circuit configured to communicate the sampled values to the second medical device, wherein the second medical device includes:

a second communication circuit configured to communicate information with the first medical device including to receive the sampled values; and a signal processing circuit configured to:

calculate a root mean square (RMS) value of amplitude of an S1 heart sound during the measurement window;

calculate a short-term central tendency of the RMS values of S1 heart sound amplitude for a time duration of N days, where N is a positive integer less than or equal to five;

calculate a long-term central tendency of the RMS values of S1 heart sound amplitude for a time duration longer than N days, wherein the long-term central tendency is calculated during different days than the short-term central tendency and at least partially prior to the short-term central tendency;

trend a long-term to short-term difference between the calculated long-term central tendency and the calculated short-term central tendency; and generate an alert using the calculated short-term central tendency and long-term central tendency.

16. The system of claim 15, wherein the first medical device is a wearable or handheld medical device and the second medical device includes a server.

17. The system of claim 15, wherein the first medical device is an implantable medical device and the second medical device is a programmer for the implantable medical device.

* * * * *